United States Patent
Skottun

[11] Patent Number: 6,117,171
[45] Date of Patent: Sep. 12, 2000

[54] ENCAPSULATED ACCOMMODATING INTRAOCULAR LENS

[76] Inventor: Bernt Christian Skottun, 273 Mather St., Piedmont, Calif. 94611-5154

[21] Appl. No.: 09/219,039

[22] Filed: Dec. 23, 1998

[51] Int. Cl.$^7$ .................................................. A61F 2/16
[52] U.S. Cl. ...................... 623/6.37; 623/6.38; 623/6.42; 623/6.13
[58] Field of Search ................... 623/6, 4, 6.11, 623/6.13, 6.37, 6.38, 6.42

[56] References Cited

U.S. PATENT DOCUMENTS

| | | |
|---|---|---|
| 4,731,078 | 3/1988 | Stoy et al. . |
| 4,790,847 | 12/1988 | Woods . |
| 4,842,601 | 6/1989 | Smith . |
| 4,888,012 | 12/1989 | Horn et al. . |
| 4,892,543 | 1/1990 | Turley . |
| 4,932,966 | 6/1990 | Christie et al. . |
| 5,489,302 | 2/1996 | Skottun . |

Primary Examiner—Dinh X. Nguyen

[57] ABSTRACT

An accommodating intraocular lens which is contained inside an encapsulating rigid shell so as to make it substantially insensitive to changes in the intraocular environment. A flexible transparent membrane divides the interior of the intraocular lens into two separate spaces containing fluid media with different refractive indices. The overall optical power of the intraocular lens may be altered by altering the curvature of the transparent membrane. The intraocular lens is equipped with haptics which extend inward into the interior of the intraocular lens and are attached to the encapsulating rigid shell in such a manner so as to be able to rotate around the place where the haptic crosses from the exterior to the interior of the intraocular lens. This allows the movement of the haptic to be transmitted to the interior of the intraocular lens where these movements are used to control the shape of the transparent membrane. By having the haptics rotate around the place where they cross the rigid shell, there need be only minimal motion at this point, which makes it possible to make the intraocular lens essentially insensitive to changes in the intraocular pressure.

19 Claims, 3 Drawing Sheets

ENCAPSULATED ACCOMMODATING INTRAOCULAR LENS

BACKGROUND

1. Field of Invention

This invention relates to intraocular lenses, specifically to such intraocular lenses as can be used to restore accommodation.

2. Description of Prior Art

Cataract surgery typically involves removing the cataractous natural lens and replacing it with an artificial intraocular lens. These artificial intraocular lenses, in most cases, have one fixed focus, or in some cases, a few fixed foci. This means that these intraocular lenses lack the natural lens' ability to accommodate. That is to say, they lack the ability to adjust their power over a continuous range. This means that they are not able to bring to a sharp focus light rays coming from objects over a continuous range of distances.

In the normal case the eye accommodates by having the ciliary muscle cause the crystalline lens to alter its shape. The amount of muscle power available is highly limited. Also, the amount of movement generated in the course of accommodation is quite small. Therefore, it is highly desireable for an accommodating intraocular lens to have high gain. By "high gain" is meant that small changes in position, shape, or force are capable of creating large changes in optical power.

In the case of an intraocular lens which accommodates by altering its shape, high gain may be achieved by utilizing different optical materials with substantially different refractive indices.

The optical power of a single spherical surface separating two materials with different refractive indices is given by the formula:

$$P = (n' - n)/r$$

where P denotes lens power, r denotes the radius of curvature of the spherical surface and n' and n denote the refractive indices in the two optical materials. This formula shows that, for a given radius of curvature, the power is proportional to the difference in refractive indices, i.e. to the difference between n' and n. In order to better realize how the magnitude of the difference in refractive indices affects the changes in lens power as a result of change in lens shape we take the derivative of this function:

$$dP/dr = -(n' - n)/r^2$$

which means that the change in lens power created by a given change in curvature (i.e. shape) is proportional to the magnitude of the difference in refractive indices across the surface. In other words, in order to obtain high gain (i.e. large change in power for small changes in surface shape) it is important to have optical materials with highly different refractive indices [i.e. to have the magnitude of (n'−n) be large].

The refractive index of the aqueous, i.e. the liquid filling the eye, is close to that of water which is about 1.33. Most fluids have refractive indices which are relatively similar to this value. This means that by relying on the interface between one of these materials and aqueous, relatively large shape changes are needed in order to significantly alter the overall power of the lens.

U.S. Pat. No. 5,489,302 to Skottun has described the use of a gas, e.g. room-air, as a refractive medium. Gases typically have a refractive index of 1.0, which is substantially different from the 1.33 of water. Thus, a lens using a gas as the optic medium may be able to generate substantial changes in optical power with the application of a relatively small force and small degrees of movement.

Additionally, using a gas has the advantage of allowing the intraocular lens to be lightweight and to have little mass. Light weight and little mass make the intraocular lens exert little stress on the delicate internal structures of the eye, thereby reducing the likelihood that the intraocular lens will cause damage to the intraocular environment.

Unfortunately, using a gas as a medium is not without difficulties. One potential problem is that a gas is compressible, thus making a lens using gas as its optic medium potentially susceptible to changes in intraocular pressure. That is to say, changes in intraocular pressure could potentially alter the optical power of such a lens.

Another potential problem is that thin and flexible membranes, such as are likely to used in a lens, may not be gas impermeable. An accommodating intraocular lens using gas as its optical medium will need to be able to have a flexible and transparent interface between the gas and another fluid medium. In order to be sufficiently flexible this interface will need to be fashioned out of a membrane. This membrane needs to be thin, transparent and flexible. Thin and flexible membranes tend not to be gas impermeable. Thus, it is possible that there will be some amount of gas exchange between the gas inside the intraocular lens and the surrounding aqueous. This may cause a net transport of gas either into (i.e. dissolved gases in the aqueous moving into the intraocular lens) or out of (i.e. gas moving from the lens into the aqueous) the intraocular lens.

ADVANTAGES

The main advantages of the present invention are:
(a) to provide an accommodating intraocular lens which may use a gas as an optical medium.
(b) to provide an accommodating intraocular lens which is insensitive, or only minimally sensitive, to changes in intraocular pressure.
(c) to provide an accommodating intraocular lens which may use a gas as an optical medium in which the gas inside the intraocular lens is separated from the surrounding aqueous in such a manner so as to prevent, or substantially limit, transfer of gas between the inside of the intraocular lens and the surrounding aqueous.
(d) to provide an accommodating intraocular lens which has high gain.

Further advantages of the present invention are to be light in weight and to have little mass. Also, it will have the advantage of being simple to insert into the eye so as to not require exceptional skills on the part of the surgeon. Additional advantages and objectives will become apparent from a consideration of the ensuing description and drawings.

DRAWING-FIGURES

REFERENCE NUMERALS IN DRAWINGS

| | |
|---|---|
| 10 anterior rigid surface | 15 anterior space |
| 20 posterior rigid surface | 25 posterior space |
| 30 flexible transparent membrane | 60 rigid side wall |
| 50 optical ray | 75 focal point |
| 70 optical axis | 90 movable inner sidewall |
| 80 inner member | 110 flexible seal |
| 100 rigid outer shell | 125 haptic |
| 120 auxiliary space | 140 pivot |
| 135 extension of haptic | 160 flexible sheet |
| 150 attachment | |

SUMMARY

An accommodating intraocular lens which has an outward rigid encapsulating surface which shields the interior of the lens from changes in the intraocular environment. The interior of the intraocular lens is divided into two separate spaces: an anterior space and a posterior space. These two spaces are separated by a transparent flexible membrane. Altering the curvature of this membrane makes it possible to alter the overall optical power of the lens. To the encapsulated intraocular lens are attached means whereby the ciliary muscle may alter the shape of the transparent membrane, thereby altering the overall optical power of the intraocular lens.

These means are so arranged as to allow the ciliary muscle to control the internal state of the intraocular lens without allowing changes in intraocular pressure to be transmitted to the interior of the intraocular lens. This is achieved by having haptics in the form of elongated members which extend into the interior of the intraocular lens and which are attached to the intraocular lens so as to be able to pivot around the point where they cross the encapsulating surface of the intraocular lens.

DESCRIPTION OF FIGS. 1 TO 9

Figure 1:
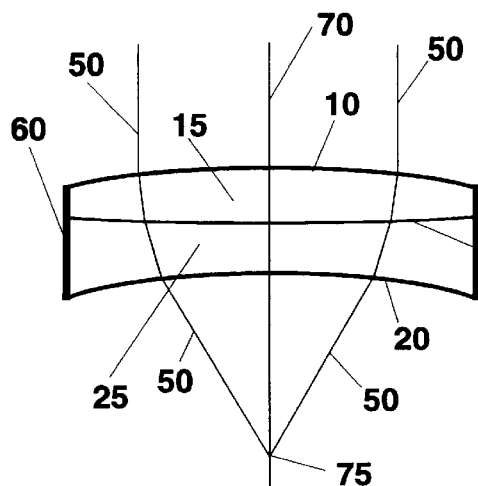
FIGS. 1A to 1B illustrate the basic principle of the encapsulated accommodating intraocular lens.
Figure 1:
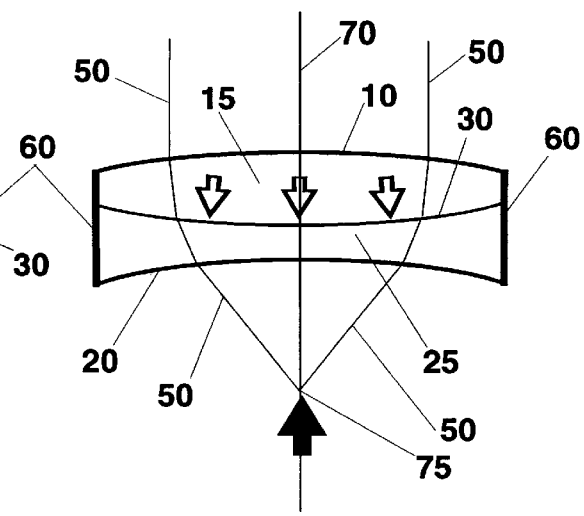

The basic principle behind the encapsulated accommodating intraocular lens is illustrated in FIG. 1A and FIG. 1B. In its most basic embodiment the encapsulated intraocular lens comprises an anterior space 15 and a posterior space 25. Anterior space 15 and posterior space 25 are separated by a flexible transparent membrane 30. Anterior space 15 and posterior space 25 together are separated from the intraocular environment outside the lens by an anterior rigid surface 10, a posterior rigid surface 20 and a rigid side wall 60. Anterior space 15 and posterior space 25 are filled with optical media having different refractive indices. In FIGS. 1A and 1B the intraocular lens is created so that the medium with the highest refractive index is in anterior space 15 and the medium with the lower refractive index is in posterior space 25. In the preferred embodiment the medium with the high refractive index has a refractive index which is higher than that of the surrounding aqueous; the other medium is assumed to have a refractive index which is lower than that of the aqueous (for example, a gas).

In FIG. 1A and FIG. 1B it can be seen that an optical ray 50 approaching the intraocular lens in a direction parallel to the optical axis 70 is refracted first as it encounters anterior rigid surface 10, then again as it encounters flexible transparent membrane 30 and finally at posterior rigid surface 20. Each of these refractions causes optic ray 50 to be deflected toward optic axis 70 in such a manner that a focal point 75 is formed.

By controlling the shape of transparent flexible membrane 30 it is possible to control the overall power of the intraocular lens (without altering the shape of either anterior rigid surface 10 or posterior rigid surface 20). For example, by making transparent flexible membrane 30 more concave, as is indicated with open arrows in FIG. 1B, the overall focal length of the intraocular lens is decreased. The decrease in focal length is shown with a filled arrow in FIG. 1B, indicating an upward displacement of focal point 75.

Figure 2:
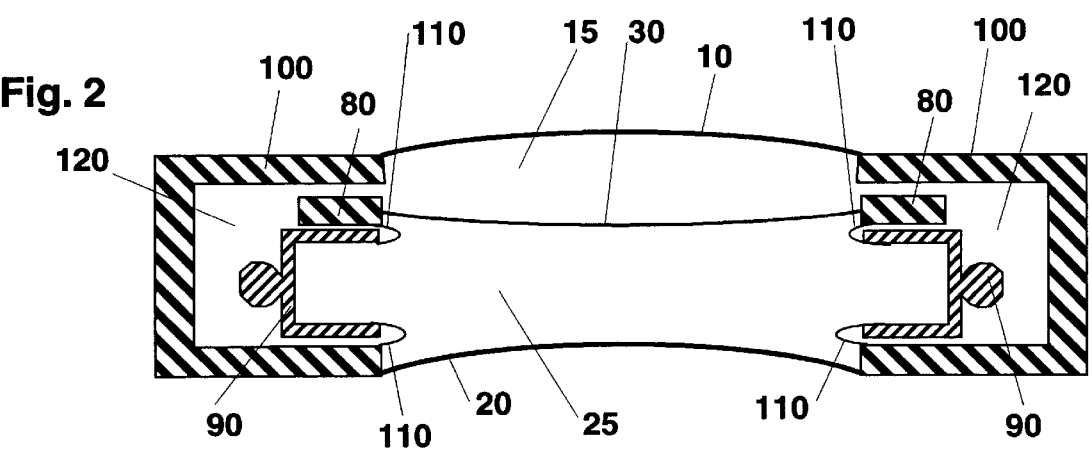
FIG. 2 shows a cross section through the encapsulated intraocular lens.

FIG. 2 shows a cross section through the preferred embodiment of the encapsulated intraocular lens. As can be seen, a pair of movable inner sidewalls 90 along with inner member 80, posterior rigid surface 20 and flexible transparent membrane 30 delineate posterior space 25. Moveable inner sidewalls 90 are fashioned so as to be able to move away from and toward the center of the lens. Movable inner sidewall 90 is connected to inner member 80 and to the inside of rigid outer shell 100 with a flexible seal 110. Flexible seal 110 prevents the medium in posterior space 25 from leaking out into auxiliary space 120 and the fluid from auxiliary space 120 from leaking into posterior space 25 while providing movable inner sidewall 90 the freedom to move.

Movable inner sidewall 90 is free to move in a radial direction away from and toward optical axis 70. In order to provide movable inner side wall 90 sufficient space to move, an auxiliary space 120 inside of rigid outer shell 100 is provided. Auxiliary space 120 is in fluid communication with anterior space 15 and is filled with the same fluid medium as anterior space 15. The communication between anterior space 15 and auxiliary space 120 allows fluid medium to be redistributed between anterior space 15 and auxiliary space 120 as movable inner side wall 90 is being displaced.

Figure 3:
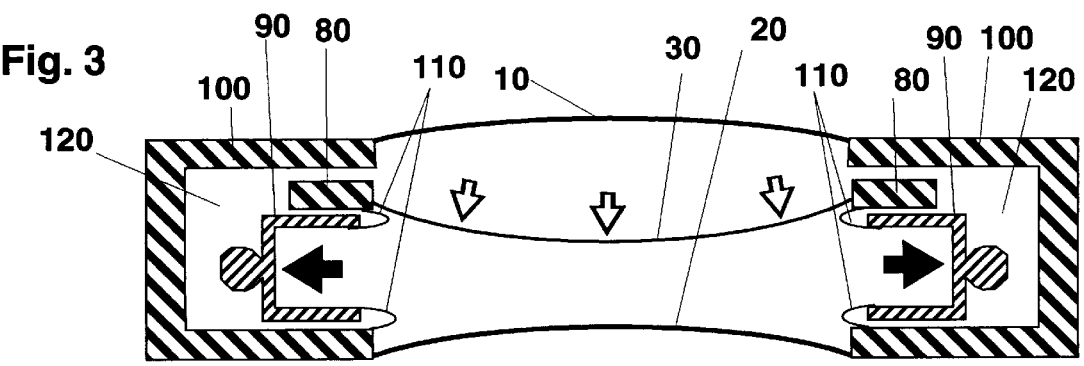
FIG. 3 shows a cross section through the encapsulated intraocular lens after it has been made to increase its power.

FIG. 3 shows the effect upon flexible transparent membrane 30 of displacing movable inner sidewalls 90 outward. The outward displacements of movable inner sidewalls 90 are indicated with filled arrows. These displacements cause flexible transparent membrane 30 to take on a more curved shape (i.e. they cause the transparent membrane to be displaced downward in FIG. 3), as indicated by the open arrows. This causes the overall power of the intraocular lens to increase. As movable inner sidewalls 90 are deflected outward, the volume of auxiliary spaces 120 is decreased. This makes fluid medium flow out of auxiliary space 120 into anterior space 15 which contributes to the downward displacement of flexible transparent membrane 30.

In order for this intraocular lens to be able to alter its power in response to changes in the ciliary muscle it is necessary that the tension in the ciliary muscle, or some intraocular structure which is controlled by the ciliary muscle, to be able to alter the position of movable inner sidewalls 90.

Figure 4:
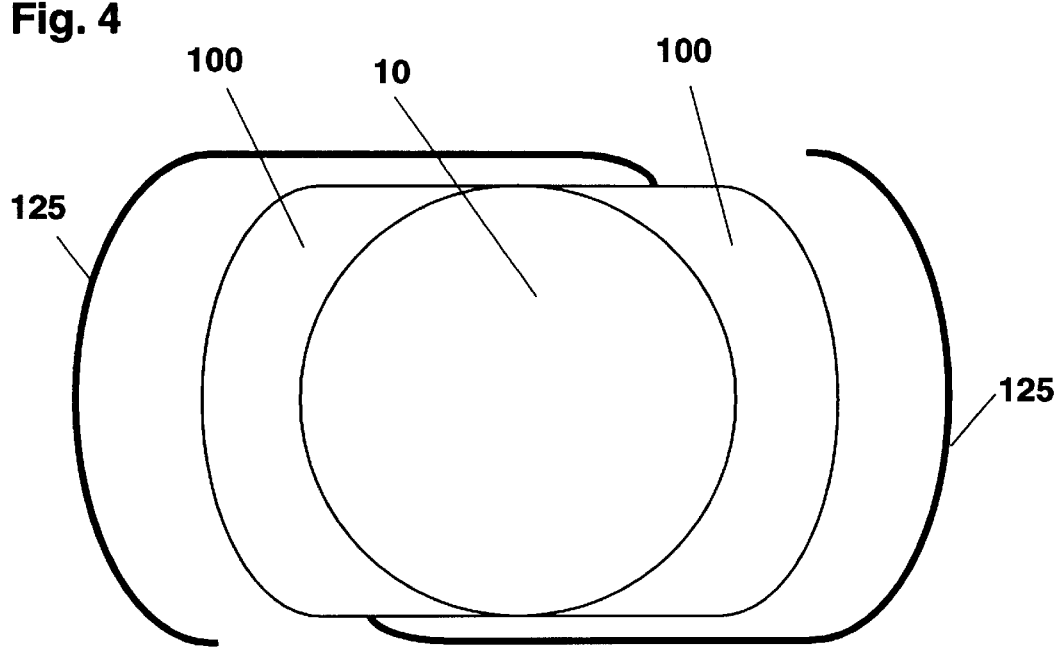
FIG. 4 shows a frontal view of the encapsulated intraocular lens.
Figure 5:
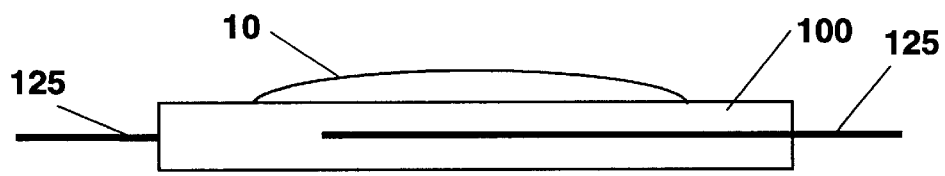
FIG. 5 shows a side view of the encapsulated intraocular lens.

FIG. 4 shows a frontal view of the encapsulated intraocular lens equipped with a pair of haptics 125. A side view of the same lens is shown in FIG. 5.

Figure 6:
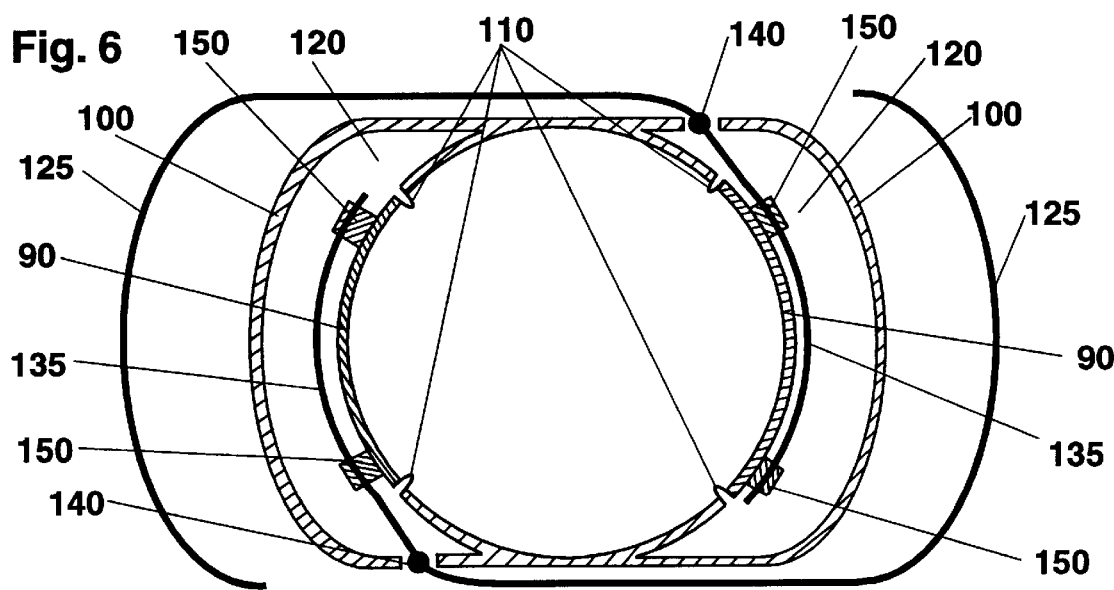
FIG. 6 shows a cross-section through the encapsulated intraocular lens in a plane perpendicular to the optical axis.
Figure 7:
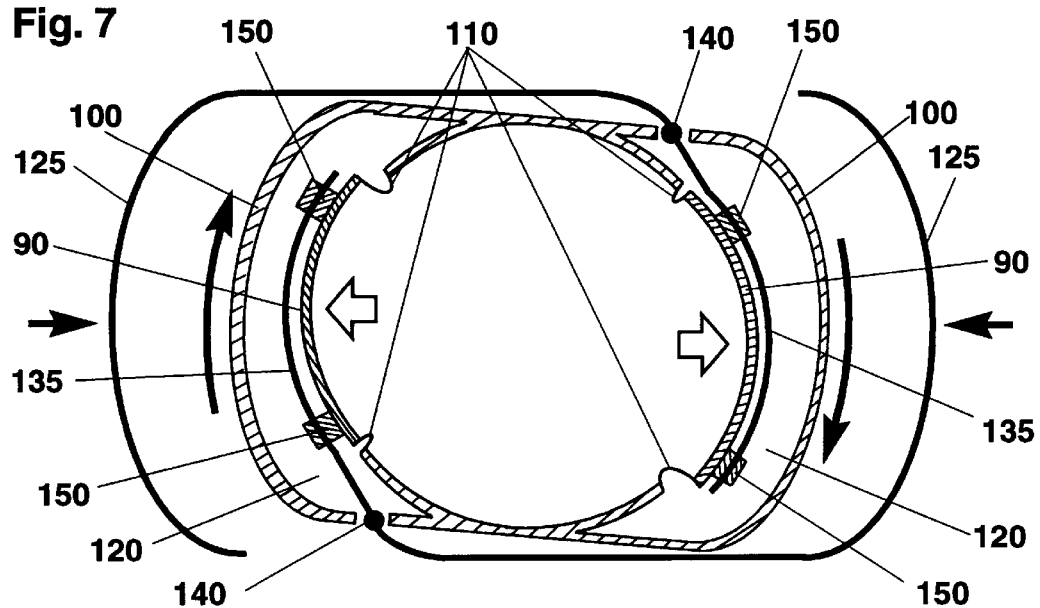
FIG. 7 shows a cross-section through the encapsulated intraocular lens as its haptics are being deflected toward the center of the lens.

The connections between haptics 125 and movable inner sidewalls 90 are shown in FIG. 6. Haptics 125 extend from outside the intraocular lens through outer rigid shell 100 into auxiliary space 120. The part extending into auxiliary space 120 has been labelled extension of haptic 135. Haptics 125 and extensions of haptics 135 are connected to rigid outer shell 100 in such a manner so as to be able to rotate around the point where haptic 125 crosses the wall of rigid outer shell 100 forming a pivot 140 at this location. Extensions of haptics 135 are attached to movable inner sidewall 90 with the use of a pair of attachments 150. The connection between haptics 125 and movable inner sidewalls 90 allows movement of haptics 125 to manipulate the position of movable inner sidewall 90. This is illustrated in FIG. 7. Straight filled arrows indicate compression of haptics 125, i.e. deflection of haptics 125 toward the center of the intraocular lens. As indicated with open arrows in FIG. 7, this causes extension of haptics 135 and movable inner sidewalls 90 to be displaced outward, i.e. away from the center of the intraocular lens. This causes flexible membrane 30 to become more concave and gives the intraocular lens increased optical power. As is indicated with long curved arrows, the compression of haptics 125 may cause the main body of the encapsulated intraocular lens to rotate somewhat in the course of the compression of haptics 125.

Figure 8:
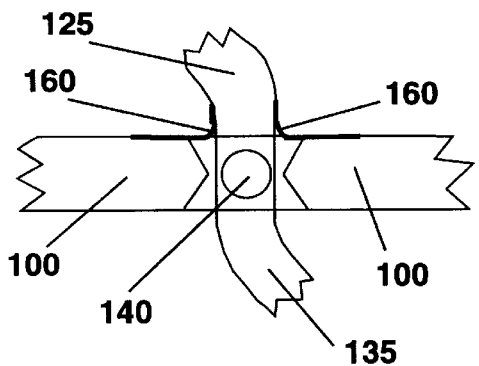
FIG. 8 shows a detail of the place where a haptic crosses the rigid outer shell.

FIG. 8 shows in more detail how haptics 125 may be able to cross the wall of rigid outer shell 100 in such manner so as to prevent, or severely limit, changes in intraocular pressure from being transmitted from the outside of the intraocular lens to the interior of the lens. Also, this arrangement prevents the fluid medium filling auxiliary space 120 from leaking out into the surrounding aqueous. Because haptic 125 pivots at the point where it crosses the wall of rigid outer shell 100 the movement at this place, as a result of displacements of haptics 125, will be minimal. This makes it easy to seal any opening in rigid outer shell with a flexible sheet 160.

Figure 9:
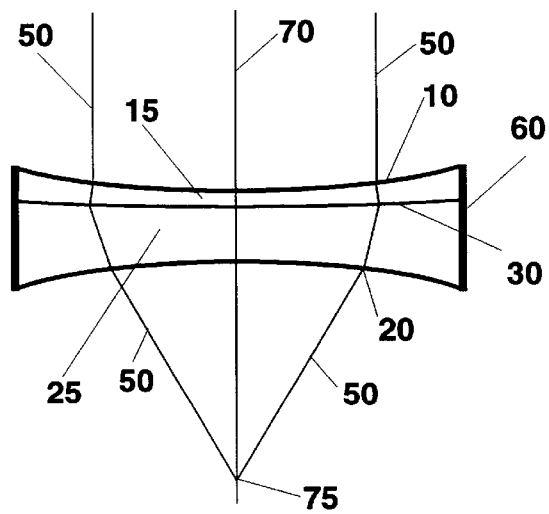
FIG. 9 shows a cross-section through an encapsulated intraocular lens which has been given an overall biconcave shape.

In the preferred embodiment of the present invention posterior space 25 is filled with a gas and anterior space 15 is filled with a heavier material with a higher refractive index. In order to make the encapsulated lens as light as possible it may be desireable to keep anterior space 15 as small as possible. As is shown in FIG. 9, in order to do so, it may be desireable to have anterior rigid surface 10 be concave. This may cause anterior rigid surface 10 to have negative lens power. However flexible transparent membrane 30 and posterior rigid surface 20 will nevertheless have positive power, which makes it possible for the overall net power of the encapsulated intraocular lens to be positive.

OPERATION

A goal of the encapsulated accommodating intraocular lens is to be able to utilize a gas as an optical medium in an accommodating intraocular lens, and to do so (1) in a manner in which changes in intraocular pressure may not alter the power of the intraocular lens by compressing any of its content, and (2) by using an arrangement in which the gas contained in the intraocular lens is separated from the aqueous so as to minimize the possibility of exchange of gas between the surrounding aqueous and the interior of the intraocular lens. The present invention seeks to achieve these two goals by encapsulating the intraocular lens using an external substantially rigid outer surface made up of anterior rigid surface 10, posterior rigid surface 20 and rigid outer shell 100. Together these parts form an enclosed space which is separated from the surrounding aqueous in such a manner that changes in intraocular pressure will not, or only minimally, be transmitted to the interior of the enclosed space. This allows the use of a compressible material, such as a gas, as a refractive medium in the intraocular lens.

With regard to the second objective, i.e. the separation of the gas inside the intraocular lens in such a manner so as to minimize the exchange of gases between the interior of the intraocular lens and the surrounding aqueous, this is addressed by having the gas filled space inside the intraocular lens, i.e. posterior space 25, be separated from the aqueous anterior space 15, posterior rigid surface 20, auxiliary space 120 and rigid outer shell 100. Anterior rigid surface 10, posterior rigid surface 20 and rigid outer shell 100 are all fashioned from substantially gas impermeable materials, and auxiliary space 120 and anterior space 15 are filled with a medium which hampers the transport of gas. Thus there is little opportunity for gas exchange between posterior space 25 and the aqueous.

A further goal of the present intraocular lens is to achieve high gain, i.e. to provide a large amount of change in optical power for small changes in the ciliary muscle of the eye. As explained above, in order to achieve this, it is desireable to have two optical media which differ as much as possible with regard to refractive index. If one of the two media is a gas, it would be desireable to have the other medium have a high refractive index, for example such as an oil.

In the preferred embodiment, as illustrated in FIGS. 2 and 3, displacements of movable inner sidewall 90 effect changes in the shape of flexible transparent membrane 30 by two different mechanisms: Firstly, this is achieved by redistributing fluid medium between auxiliary space 120 and anterior space 15. Secondly, a displacement of movable inner sidewall 90 directly causes a change in curvature of flexible transparent membrane 30 in order for the volume of posterior space 25 to remain unaltered as movable inner side walls 90 are displaced. Together these two mechanisms form an effective push-pull arrangement.

The encapsulated accommodating intraocular lens is intended to be placed in the emptied lens capsule. Typical cataract surgery involves extracapsular extraction. This leaves the lens capsule available for housing the artificial intraocular lens. The lens capsule is connected to the ciliary body and thus the ciliary muscle with a series of zonules, also know as suspensory ligaments. These zonules transmit changes in ciliary muscle tension to the lens capsule. When the ciliary muscle is relaxed the zonules are taut, thus pulling the equator of the lens capsule outward causing it to be flattened. Increased tension in the ciliary muscle reduces the tension in the zonules, thus allowing the lens capsule to contract. This contraction will increase the tension exerted on haptics 125 from the lens capsule. This deflects haptics 125 inward, which causes movable inner sidewall 90 to be deflected outward; this in turn causes flexible transparent membrane 30 to become more curved, which causes the lens to increase its lens power as described above. In this manner increased tension in the ciliary muscle causes the lens to increase its power.

In order for changes in the ciliary muscle to be able to be transmitted to the interior of the intraocular lens at least one haptic 125 is connected to elongated inner member 80 in such a manner that movement in haptic 125 will be transmitted to inner member 80. Haptic 125 and inner member 80 are attached to each other and are together attached to rigid side wall 60 in such a manner as to be able to pivot around the place at which inner member 80 crosses rigid side wall 60. This makes it possible for movement to be transmitted from the outside of the intraocular lens to the interior of the intraocular lens with minimal movement at the point where inner member 80 crosses rigid side wall 60. Because the amount of movement at this place will be very small it will be possible to effectively seal the openings in rigid side wall 60 around the point where inner member 80 crosses rigid side wall 60 using flexible sheet 160 which needs to cover only a small area and needs only to be flexible to a minor degree. This means that changes in the intraocular pressure have only a small opportunity to be transmitted to the interior of the intraocular lens at this place. This makes it possible for the intraocular lens to be substantially insensitive to changes in intraocular pressure.

CONCLUSION, RAMIFICATION AND SCOPE

Accordingly, the reader will see that the encapsulated accommodating intraocular lens of this invention can be used to restore accommodation in a human eye. Furthermore the intraocular lens has the advantages that it is substantially unaffected by changes in intraocular pressure;

it can be made so as to present a substantially gas-impermeable outer surface to the surrounding aqueous;

it has high gain;

it is of light weight;

it is compatible with currently established surgical procedures for cataract extraction and intraocular lens implantation.

Although the description above contains many specificities, these should not be construed as limiting the scope of the invention but as merely providing illustrations of some of the presently preferred embodiments of this invention. The scope of the invention should be determined by the appended claims and their legal equivalents, rather than by the examples given.

I claim:

1. An intraocular lens comprising an encapsulating outer surface, at least a part of said surface being transparent, said encapsulating surface forms an internal cavity, said internal cavity contains an internal optical element, said internal optical element has the ability to vary its optical power, to said intraocular lens is attached at least one haptic, said haptic have the shape of an elongated member, said haptic is located outside of said intraocular lens, to said haptic is attached firmly an elongated inner member, said inner member extends into the interior of said intraocular lens, said inner member and said haptic together are able to rotate around the point where said inner member crosses from the outside of said intraocular lens to the interior of said intraocular lens allowing movement of said haptic to be transmitted to the parts of said inner member which are located inside said intraocular lens, said haptic is equipped with means whereby the movement of said inner member may alter the lens power of said internal optical element, thereby allowing movement of said haptic to control the lens power of said inner optical element thereby controlling the overall optical power of said intraocular lens.

2. An intraocular lens as described in claim 1 in which said intraocular lens contains a gas.

3. An intraocular lens as described in claim 1 in which some part of the elongated member is in contact with the lens capsule of the eye.

4. An intraocular lens as described in claim 1 in which the power of said intraocular lens is substantially controlled by the tension in the ciliary muscle.

5. An intraocular lens as described in claim 1 in which the power of said intraocular lens is substantially controlled by the position of said elongated member.

6. An intraocular lens as described in claim 1 in which the power of said intraocular lens is substantially altered by changes in the force exerted by the lens capsule onto said elongated member.

7. An intraocular lens comprising an encapsulating outer surface, at least part of said surface being transparent, said encapsulating surface forms an internal cavity, said internal cavity contains an internal optical element, said internal optical element has the ability to vary its optical power, said internal element is connected to at least one elongated member, one end of said elongated member being inside of said internal cavity, the other end of said elongated member being outside of said encapsulating outer surface, said elongated member is attached to said encapsulating outer surface in such a manner so that said member has some freedom to pivot around the point where said member crosses said encapsulating outer surface.

8. An intraocular lens as described in claim 7 in which said intraocular lens contains a gas.

9. An intraocular lens as described in claim 7 in which said intraocular lens contains a medium which is substantially impermeable to gases.

10. An intraocular lens as described in claim 7 in which some part of said elongated member is attached to a haptic, said haptic being in direct contact with an anatomical structure in the eye.

11. An intraocular lens as described in claim 7 in which the power of said intraocular lens is substantially controlled by the tension in the ciliary muscle.

12. An intraocular lens as described in claim 7 in which the power of said intraocular lens is substantially controlled by the position of said elongated member.

13. An intraocular lens as described in claim 7 in which the power of said intraocular lens is substantially altered by changes in the force exerted by the lens capsule onto said elongated member.

14. An intraocular lens comprising an encapsulating outer surface, at least part of said encapsulating surface being transparent, said encapsulating surface forms an internal cavity, said internal cavity being divided into an anterior space and a posterior space by a flexible transparent membrane, said anterior space and said posterior space being filled with transparent fluid media having different refractive indices, to said intraocular lens is attached at least one elongated member, one end of said elongated member is located inside of said encapsulating surface, the other end of said elongated member is located outside of said encapsulating outer surface, said elongated member is attached to said encapsulating outer surface in such a manner so that said member has some freedom to pivot around the point where said member crosses said encapsulating outer surface, and means whereby the position of said member may alter the shape of said flexible membrane so as to alter the optical power of said intraocular lens.

15. An intraocular lens as described in claim 14 in which said intraocular lens contains a gas.

16. An intraocular lens as described in claim 14 in which some part of the elongated member is in contact with the lens capsule of the eye.

17. An intraocular lens as described in claim 14 in which the power of said intraocular lens is substantially controlled by the tension in the ciliary muscle.

18. An intraocular lens as described in claim 14 in which the power of said intraocular lens is substantially altered by changes in the force exerted by the lens capsule onto said elongated member.

19. An intraocular lens as described in claim 14 in which the end of said elongated member which is located outside of said intraocular lens serves as a haptic to attach said intraocular lens to an anatomical structure inside an eye.

\* \* \* \* \*